United States Patent [19]

Parker

[11] Patent Number: 5,038,766
[45] Date of Patent: Aug. 13, 1991

[54] BLIND OROLARYNGEAL AND OROESOPHAGEAL GUIDING AND AIMING DEVICE

[76] Inventor: Jeffrey D. Parker, 2219 Grandin Rd., Cincinnati, Ohio 45208

[21] Appl. No.: 433,687

[22] Filed: Nov. 8, 1989

[51] Int. Cl.$^5$ .................... A61M 16/00; A61B 1/26
[52] U.S. Cl. .................... 128/200.26; 128/10
[58] Field of Search .................... 128/10, 11, 200.26, 128/207.14, 207.15, 911, 912, 4, 15, 16; 604/23

[56] References Cited

U.S. PATENT DOCUMENTS

| | | | |
|---|---|---|---|
| 3,754,554 | 8/1973 | Felbarg | 128/200.26 |
| 3,756,244 | 9/1973 | Kinnear et al. | 128/207.14 |
| 3,802,440 | 4/1974 | Salem et al. | 128/200.26 |
| 3,874,377 | 4/1975 | Davidson | 128/207.15 |
| 3,908,665 | 9/1975 | Moses | 128/207.14 |
| 3,930,507 | 1/1976 | Berman | 128/207.14 |
| 3,948,255 | 4/1976 | Davidson | 128/207.14 |
| 4,068,658 | 1/1978 | Berman | 128/200.26 |
| 4,155,365 | 5/1979 | Boslau | 128/207.15 |
| 4,166,468 | 9/1979 | Haynie | 128/207.15 |
| 4,167,946 | 9/1979 | Sandstrom | 128/207.17 |
| 4,211,234 | 7/1980 | Fisher | 128/200.26 |
| 4,231,365 | 11/1980 | Scarberry | 128/207.15 |
| 4,256,099 | 3/1981 | Dryden | 128/200.26 |
| 4,338,930 | 7/1982 | Williams | 128/200.26 |
| 4,365,625 | 12/1982 | Rind | 128/207.14 |
| 4,497,318 | 2/1985 | Donmichael | 128/202.28 |
| 4,509,514 | 4/1985 | Brain | 128/207.15 |
| 4,612,927 | 9/1986 | Kruger | 128/200.26 |
| 4,655,214 | 4/1987 | Linder | 128/207.18 |
| 4,672,960 | 6/1987 | Frankel | 128/200.26 |
| 4,683,879 | 8/1987 | Williams | 128/200.26 |
| 4,685,457 | 8/1987 | Donenfeld | 128/207.14 |
| 4,773,394 | 9/1988 | Reichstein et al. | 128/4 |
| 4,825,858 | 5/1989 | Frankel | 128/200.26 |
| 4,832,020 | 5/1989 | Augustine | 128/207.14 |
| 4,840,172 | 6/1989 | Augustine et al. | 128/207.14 |
| 4,919,126 | 4/1990 | Bailden | 128/207.14 |

FOREIGN PATENT DOCUMENTS

| | | |
|---|---|---|
| 2489686 | 9/1981 | France . |
| 2137096 | 10/1984 | United Kingdom . |
| 2205499 | 12/1988 | United Kingdom . |
| 2229367 | 9/1990 | United Kingdom . |

OTHER PUBLICATIONS

Leroy, Recherches Sur l'Asphyxie, 7 J. de Physiologique, 45 65, 1827 (with translation).
Knapp, Medical Record, N.Y., 322, Aug. 29, 1896.
Understanding Anasthesia Equipment, pp. 342-343 and 346-349.
Fundamentals of Tracheal Intubation, pp. 74-76 and FIGS. 4-9, at p. 56.
Machida Nasopharyngo-Laryngoscope.
Anasthesiology Review, p. 24, vol. VIII, No. 1.
Rusch Super Safety Clear Endotracheal Tubes.
"British Journal of Anaesthia" The Laryngeal Mask-A New Concept in Airway Management; 1983; vol. 55; pp. 801-805.
"Anasthesia"; Three Cases of Difficult Intubation Overcome by The Laryngeal Mask Airway; 1985; vol. 40; pp. 353-355.
"Anasthesia"; The Laryngeal Mask Airway; 1985; vol. 40, pp. 356-361.

Primary Examiner—Edgar S. Burr
Assistant Examiner—Eric P. Raciti
Attorney, Agent, or Firm—Wood, Herron & Evans

[57] ABSTRACT

The present invention relates to a medical device which facilitates rapid, accurate, blind access to the larynx and/or esophagus such as for emergency intubation of a patient's trachea and simultaneous suctioning of the hypopharynx or esophagus. Disclosed is a disposable, one-piece, anatomically contoured guide element having a channel therethrough, the guide element being releasably mounted at the end of a curved blade and handle, which is used to blindly insert the guide element into the throat. When properly seated in the pharynx and hypopharynx, the guide element is positioned about and atop the larynx such that the wall of the channel forms a substantially gap-free junction with and upward continuation of the tubular wall of the laryngeal opening so that an orotracheal tube advanced downward through the channel will be guided exclusively into the larynx and trachea without substantial risk of accidental intubation of the esophagus or other areas of the hypopharynx. Also disclosed are provision of tunnels through the guide element for blindly guiding and/or aiming other tubular-type members into the esophagus or larynx as desired.

78 Claims, 7 Drawing Sheets

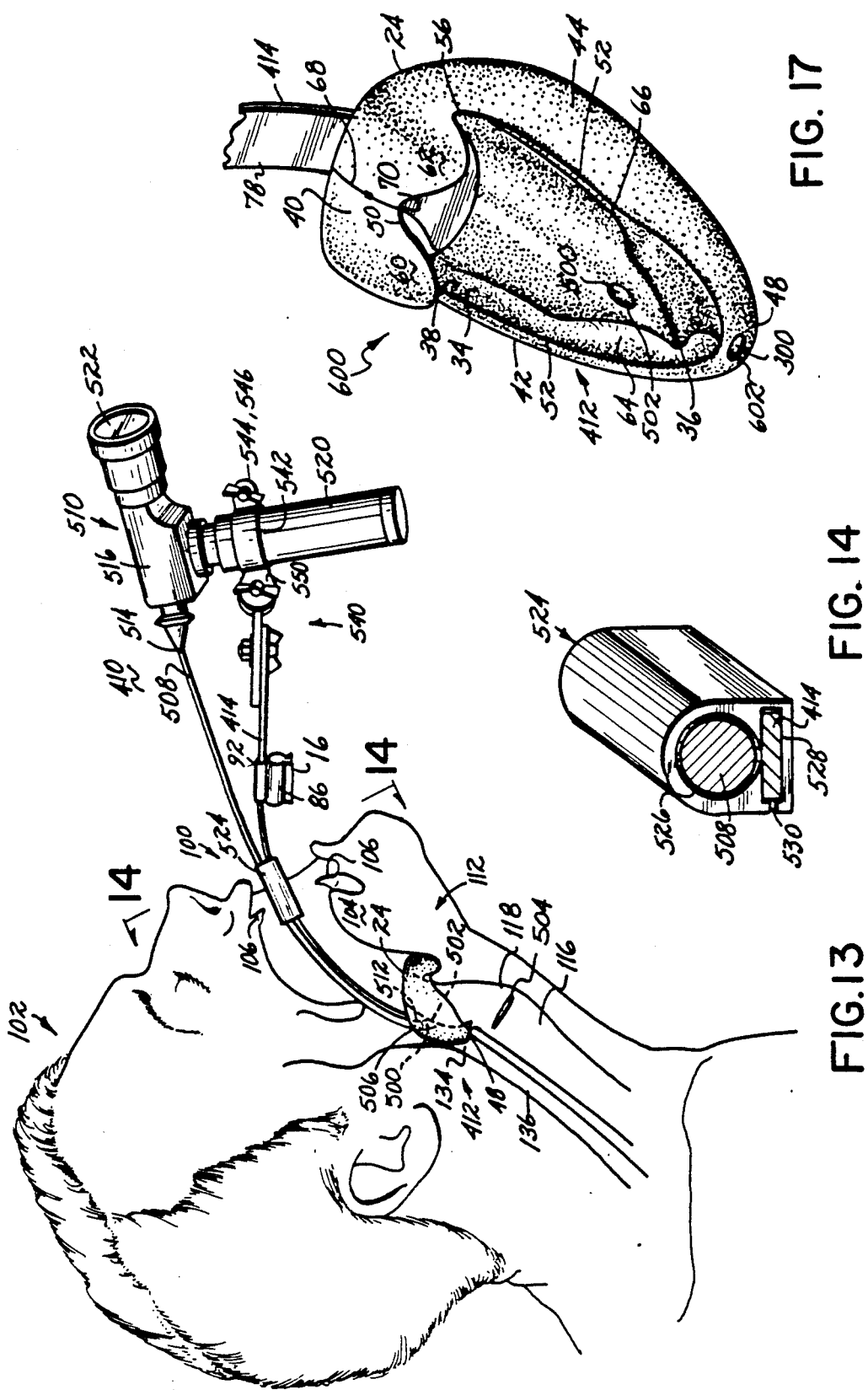

BLIND OROLARYNGEAL AND OROESOPHAGEAL GUIDING AND AIMING DEVICE

BACKGROUND OF THE INVENTION

I. Field of the Invention

The present invention relates to a medical device which blindly and selectively facilitates the rapid, gentle and accurate guiding, aiming, and stabilizing of tubular or elongated members relative to the larynx and esophagus of humans and animals, especially under emergency conditions. The present invention further relates to such a device to facilitate rapid, gentle, blind oral intubation of the larynx or esophagus for purposes of ventilation, suctioning, inspection with a fiberoptic endoscope, forceps retrieval of foreign bodies, or remote biopsy, as desired.

II. Description of the Prior Art

As is well known, breathing and swallowing are accomplished through respective canals which open at the back of throat (the pharynx). One such canal extends through the larynx and trachea to the lungs to allow breathing. The other canal extends through the esophagus to the stomach for passage of food. The openings to the larynx and esophagus are positioned very close together. That positioning, along with other closely adjacent anatomical spaces at the back of the throat, presents difficulties to a medical provider needing to obtain rapid, specific access to a selected one of the canals, particularly in emergency situations.

For example, when a patient stops breathing, it is imperative that effective ventilation be instituted as soon as possible. Ventilation is best accomplished by forcing air through an orotracheal tube inserted through the mouth and laryngeal opening and into the trachea. Current methods of orotracheal intubation, the process of inserting the tube, are frequently slow and difficult, and prone to life-threatening error. The considerable angle between the axes of the mouth and larynx, and the intervening presence of the tongue and epiglottis, make it impossible to see the larynx through the mouth without special positioning and instrumentation. Also, there is ample space around the larynx into which an orotracheal tube can be easily and unwittingly misdirected. Indeed, it is not uncommon for the tube to be accidently inserted into anatomical spaces surrounding the larynx, such as the closely adjacent esophagus, rather than the larynx. Similarly, it is sometimes necessary to introduce a suction catheter at or into the esophageal opening to evacuate vomitus from the throat prior to orotracheal intubation. But, such a catheter can be accidently inserted into the larynx and trachea instead.

Whether ventilation of the lungs or suctioning along the oroesophageal axis is desired, prior art devices and methods do not assure the exclusive passage of the tubular member into the intended orifice (of the larynx or esophagus). The major danger is that if the tubular member is incorrectly placed, attempts to ventilate or suction the patient may instead result in suffocation. In a non-breathing patient, for example, if ventilation is supplied to the stomach rather than to the lungs through an orotracheal tube which has been accidentally introduced into the esophagus instead of the trachea, the stomach will inflate while the lungs receive no air and the patient will suffocate. Similarly, if suction is applied to a catheter which has been accidentally introduced into the trachea instead of the esophagus, the air in the trachea and lungs will be evacuated and the patient will suffocate. Thus, there is a need for an accurate means to direct tubes rapidly and selectively into the intended openings of either the larynx or esophagus.

One known method of guiding an orotracheal tube involves inserting a finger into the patient's throat and, using the sensation of touch, guiding the orotracheal tube down into the laryngeal opening. This is a "blind" method, in that the medical provider does not see the larynx when placing the tube. However, this blind, tactile method of intubation is not favored, and often results in accidental intubation of the esophagus instead of the trachea, frequently with tragic consequences. An instrumentguided method of blind intubation was developed in France by Leroy in 1827. But Leroy's two-bladed intubation speculum lacked any means to prevent accidental intubation of the esophagus or other areas adjacent to the larynx.

In 1912, a non-blind method of orotracheal intubation was developed using a blade laryngoscope to expose the larynx and allow the intubationist to "see" where to insert the orotracheal tube. This non-blind (or "visual") laryngoscopic method of orotracheal intubation was quickly accepted by the medical community as a logical way to eliminate the errors and complications inherent in blind intubation, and has become the method of choice for orotracheal intubation in the emergency setting.

Unfortunately, laryngoscopic orotracheal intubation has not only failed to eliminate accidental misintubation, but has introduced its own set of serious limitations and complications, sometimes catastrophic. For example, blade laryngoscopes, the devices used most for emergency orotracheal intubation, nearly always require that the laryngoscopist be positioned above the head of the patient to be intubated, and that the patient be lying in a supine position with mouth opened widely and neck extended so as to straighten the oral-pharyngeal-laryngeal axis in order to permit a transoral view of the larynx so that a tube may be inserted thereinto. But such relative positioning of the patient and laryngoscopist is frequently unachievable, where for example, the patient is trapped in an awkward position inside a wrecked vehicle. Similarly, the patient's mouth may not be widely openable where, for example, the temporomandibular joint is ankylosed or the jaw is broken; and extending the patient's neck may cause or aggravate a cervical spine injury. Another problem with laryngoscopic intubation is that substantial force must be applied via the rigid blade of the laryngoscope to depress the tongue and pull the epiglottis forward far enough to obtain a view of the larynx. This force frequently results in teeth being broken by the laryngoscope blade, and occasionally results in bleeding in the throat. Such bleeding can be uncontrollable in patients with thrombocytopenia or other bleeding disorders, and can prevent an adequate view of the larynx, thus hindering the attempt to intubate. A further problem is that during laryngoscopic intubation, there is no satisfactory way to prevent vomitus from rising from the esophagus into the throat, where it can obscure a view of the larynx, impairing the attempt to intubate, and where it can also be aspirated into the trachea and lungs, causing aspiration pneumonia and impairing effective ventilation. The presence of substantial blood, vomitus, or other debris in the throat currently requires that a suction catheter be introduced into the throat to evacuate these larynx-obscuring substances. But pausing to suction the throat delays intubation, since the suction catheter itself frequently obscures the view through the laryngoscope and interferes with manipulation of the orotracheal tube in the throat. Thus, orotracheal intubation cannot proceed easily and safely until the suction catheter is removed from the throat—at which time, further bleeding or vomiting may necessitate its reintroduction.

Another problem is that the technique of laryngoscopic intubation requires considerable training, skill, and experience before a high rate of success can be expected. One or more assistants are frequently needed by the laryngoscopist to perform ancillary tasks such as holding the patient's neck in an extended position, pressing externally on the larynx, and suctioning the throat. A further problem is that metal laryngoscopes are relatively expensive to buy and maintain. Perhaps the greatest imperfection of blade laryngoscopes is that they do not assure accurate orotracheal intubation. Even the laryngoscopes which substitute long, flexible or malleable fiberoptic image guides for rigid blades have major disadvantages. For example, they are very expensive, fragile, difficult to learn to use, slow in actual use, frequently require the use of an assistant, and have no reliable way to rapidly achieve correct and stable orolaryngeal positioning of their distal tips. Several attempts have been made to supersede the laryngoscope with devices which purport to facilitate blind intubation. But these devices have never overcome the principal problem of Leroy's device and of blade laryngoscopes, in that they have provided no safe and effective means to assure accurate orotracheal intubation.

OBJECTS OF THE INVENTION

Thus, there is a need for a device for emergency orotracheal intubation which overcomes the above problems. Specifically, such a device should facilitate rapid orotracheal intubation of patients regardless of their position with respect to the intubationist, and without opening the mouth widely or extending the neck. The device should not require the application of substantial force within the mouth or throat. It should prevent or remove the accumulation of vomitus (or blood or mucus) in the throat during intubation. Alternatively, the device should facilitate blind orotracheal intubation which will not be hindered by the presence of larynx-obscuring vomitus, blood, or mucus. The device should be relatively inexpensive to buy and maintain, simple to use, easy to learn and teach, and equipped with safe and effective means to minimize the risk of misintubation. It should also be capable of rapidly and blindly aiming the forward tip of the fiberbundle of a fiberoptic laryngoscope into the larynx with a high degree of accuracy and stability so that emergency visual orotracheal intubation using such laryngoscopes will become feasible. It should also facilitate the rapid placement of other tubular or elongated members, such as grasping and biopsy forceps, into or adjacent the laryngeal or esophageal openings for examination or treatment of the patient.

SUMMARY OF THE INVENTION

The present invention provides for safe and rapid placement of a tubular or elongated member relative the desired anatomical opening at the back of the throat without the drawbacks encountered in the prior art. In its broadest sense, the present invention provides a guide element receivable through the mouth and into the back of the throat, the guide element having an annulus portion with a channel defined by a channel wall extending through the annulus portion, the guide element further having anatomically contoured surfaces which cooperate with corresponding anatomical features (processes and recesses) at the back of the throat to stabilize the guide element in a relatively fixed position within the throat such that the channel wall of the guide element is aligned and substantially continuous with the tubular wall of the laryngeal opening to define a substantially exclusive airway path extension atop and coaxial the larynx. During insertion of the guide element, anatomically contoured surfaces on the guide element also act to stop rearward progress of the guide element as it is pushed into the throat so that the channel does not overrun the larynx. The guide element is preferably comprised of a soft semi-flexible material so as not to traumatize the throat.

The airway path extension may function as a tube guideway through which a tubular or elongated member may be passed into or aimed at the laryngeal opening. The guide element may further be utilized to guide or aim such a member into the esophageal opening via a separate tunnel through the guide element. When so utilized, the airway path extension further provides a mechanism to maintain breathability of the patient during esophageal intubation.

The present invention further contemplates provision of a blade member, preferably curved to conform generally to the curvature between the mouth and the larynx, by which to insert the guide element through the patient's mouth and into the back of the throat. Preferably, the distal end of the blade is coupled to the guide element such that the guide element may be moved within the throat by manipulation of a handle at the proximal end of the blade member outside the mouth. As the guide element approaches the back of the throat, the anatomical mating surfaces of the guide element cooperate with the anatomical features at the back of the throat to achieve the desired alignment. As a consequence, the guide element may be blindly yet properly positioned in the patient's throat.

In accordance with one aspect of the invention, blind orotracheal intubation may be safely and rapidly accomplished. To this end, certain of the anatomically contoured surfaces of the guide element preferably surround the laryngeal opening and embrace the larynx at a substantially gap-free junction such that the airway path extension is defined substantially exclusively between the larynx and the upper surface of the annulus portion of the guide element. As a consequence, an orotracheal tube inserted into the channel of the annulus portion will not readily pass into any other anatomical space at the back of the throat except the opening into the larynx, thus minimizing the possibility of misintubation. The guide element further preferably includes a body portion depending from the rear of the annulus portion, the body portion including a bearing surface defining an extension of the posterior wall of the channel along which an orotracheal tube may bear as it travels through the guide element and whereby the tube is directed properly towards the larynx. The bearing surface desirably includes a projecting cusp aimed into the laryngeal opening to prevent overtravel of the tube into the rear edge of the larynx or beyond the back of the larynx and to center the guide element. Preferably, the cusp extends into the interarytenoid incisure in the posterior edge of the laryngeal opening.

The distal tip of an orotracheal tube is preferably releasably held in the channel prior to insertion of the guide element into the patient's mouth. As the guide element is inserted, the remainder of the tube extends out of the mouth. The guide element is easily, gently, and rapidly seated at the back of the throat, after which intubation is safely, rapidly and reliably accomplished merely by slidably advancing the tube further into the guide element whereupon it travels downward through the channel and is guided properly along the bearing surface toward and into the larynx. The guide element thus acts to guide the orotracheal tube while substantially reducing the risk of accidently intubating the esophagus or other areas adjacent the larynx.

In accordance with a further aspect of the invention, the body portion of the guide element preferably terminates at an occluding wall or tip below the bearing wall. The occluding wall is positioned relative the channel to overlie and substantially occlude the esophageal opening so as to block the passage of vomitus upward from the esophagus into the throat and larynx during intubation and to help prevent any tubular or elongated member inserted into the mouth after the guide element is seated from being accidently passed into the esophagus. Still further, the annulus portion of the guide element forward of the bearing wall preferably extends beyond the larynx to overlie anatomical features therearound so as to further minimize the risk of accidentally passing a tubular or elongated member, such as an orotracheal tube, into anatomical spaces surrounding the larynx.

In accordance with a yet further aspect of the present invention, esophageal intubation may also be readily accomplished with an esophageal tunnel through the body portion of the guide element. The body portion extends toward the esophagus such that the occluding wall or tip of the body portion preferably lies immediately above the esophageal opening. The tunnel passes through the body portion between the occluding wall and the edge of the annulus portion upper surface. The esophageal tunnel is positioned relative the channel such that when the channel is aligned with the laryngeal lumen, the esophageal tunnel is aligned and in close communication with the esophageal opening to define a substantially continuous path between the esophagus and the upper surface of the guide element. Preferably, the bearing surface creates a wall between the esophagus tunnel and the channel to prevent communication therebetween whereby to minimize the possibility of erroneously inserting into the larynx a tube or other elongated member intended for the esophagus and vice versa. Moreover, provision of the channel provides an airway path to permit continued patient breathing and/or a tube guideway for orotracheal intubation if necessary while or in conjunction with intubating the esophagus so as not to accidentally suffocate the patient.

An elongated or tubular member, such as a suction catheter, forceps or the distal viewing end of a fiberbundle of a flexible fiberoptic laryngoscope, is receivable through the esophagus tunnel for passage into or toward the esophagus. The distal end of such a member may be releasably held in the tunnel prior to insertion of the guide element into the patient's mouth. The guide element is easily and rapidly inserted into and seated in the throat while the remainder of the elongated or tubular member extends out of the mouth. After the guide element is seated at the back of the throat, the tubular-type member may then be advanced into the esophagus, if desired, by pushing it further into the guide element such that the distal end passes beyond the tip of the guide element and into the esophagus.

In conjunction with the blade member, the desired tubular or elongated member(s) may be held to the guide element by a clip or the like which holds the tubular-type member against the blade member with the distal end of the tubular-type member releasably held in the guide element. After seating of the guide element in the throat, the tubular-type member may be released from the clip and advanced into the larynx or esophagus as appropriate. Thereafter, the guide element may be withdrawn from the throat leaving behind the intubated tubular-type member. To allow for removal of the guide element over the tubular-type member, the guide element may be provided with a separable slit extending between the exterior surface of the guide element and the channel, for example.

In accordance with a further aspect of the present invention, a flexible or stylet-type fiberoptic laryngoscope may be rapidly and reliably aimed to allow visual examination of the larynx. In accordance with this aspect of the invention, a slant tunnel is provided in the guide element terminating in the airway path extension defined by the channel. The distal viewing end of a fiberbundle of the laryngoscope may be releasably secured in the slant tunnel of the guide element to provide a sight mechanism into the larynx upon seating of the guide element in the back of the throat. All the while, the channel maintains an airway path extension so as not to interfere with patient breathing. Additionally, an orotracheal tube may be advanced through the channel to accomplish orotracheal intubation if necessary. Yet further, esophageal intubation may be accomplished with an esophageal tunnel passing through the body portion as previously described.

A portion of the fiberbundle between the distal viewing end and the eyepiece end may be held against the blade member by a protective clip which protects the fibers from damage by the teeth. Further, the proximal end of the blade member may be provided with a support structure for supporting a laryngoscope body to which the fiberbundle eyepiece end is connected. In the latter event, the laryngoscope body may also serve as the handle for the blade member.

By virtue of the foregoing, there is thus provided a guiding and aiming device to facilitate blind, gentle, rapid, accurate and selective guiding and aiming of tubular or elongated members relative a patient's larynx and esophagus, especially under emergency conditions. There is thus further provided a guiding and aiming device to facilitate blind, gentle, rapid, accurate, and selective intubation of the larynx and/or esophagus, substantially without risk of misintubation and without the drawbacks of the prior art. That is, using a guide element according to the principles of this invention, tubular or elongated members may be blindly and selectively aimed or introduced into the laryngeal or esophageal openings, in a rapid, gentle and reliable manner.

More specifically, intubation with the guiding and aiming device requires only a few seconds to accomplish; requires only a soft, semi-flexible guide element to be in contact with the patient's throat; is simple to use; is easy to learn and teach; is relatively inexpensive; does not require that the intubationist be positioned above the head of the patient, or that the patient's mouth be opened widely, or that the patient's neck be extended, or that assistants be present, or that substantial force be applied within the mouth or throat, or that larynxobscuring fluids be suctioned out of the throat prior to intubation, or that a view of the larynx be secured; provides means to minimize the risk of misintubation; and is, thus, far more versatile and considerably safer than the currently accepted method of intubation with blade laryngoscopes.

These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

FIG. 13 is a schematic illustration, partially cut-away, showing a further embodiment of a medical device in accordance with the principles of the present invention stabilized in the throat of a patient for laryngoscope aiming;

FIG. 14 is a front perspective view of the bite protector clip of FIG. 13 along line 14—14 thereof;

FIG. 17 is a perspective view of an alternative embodiment of a guide element according to the principles of the present invention.

DETAILED DESCRIPTION OF THE DRAWINGS

Figure 1:
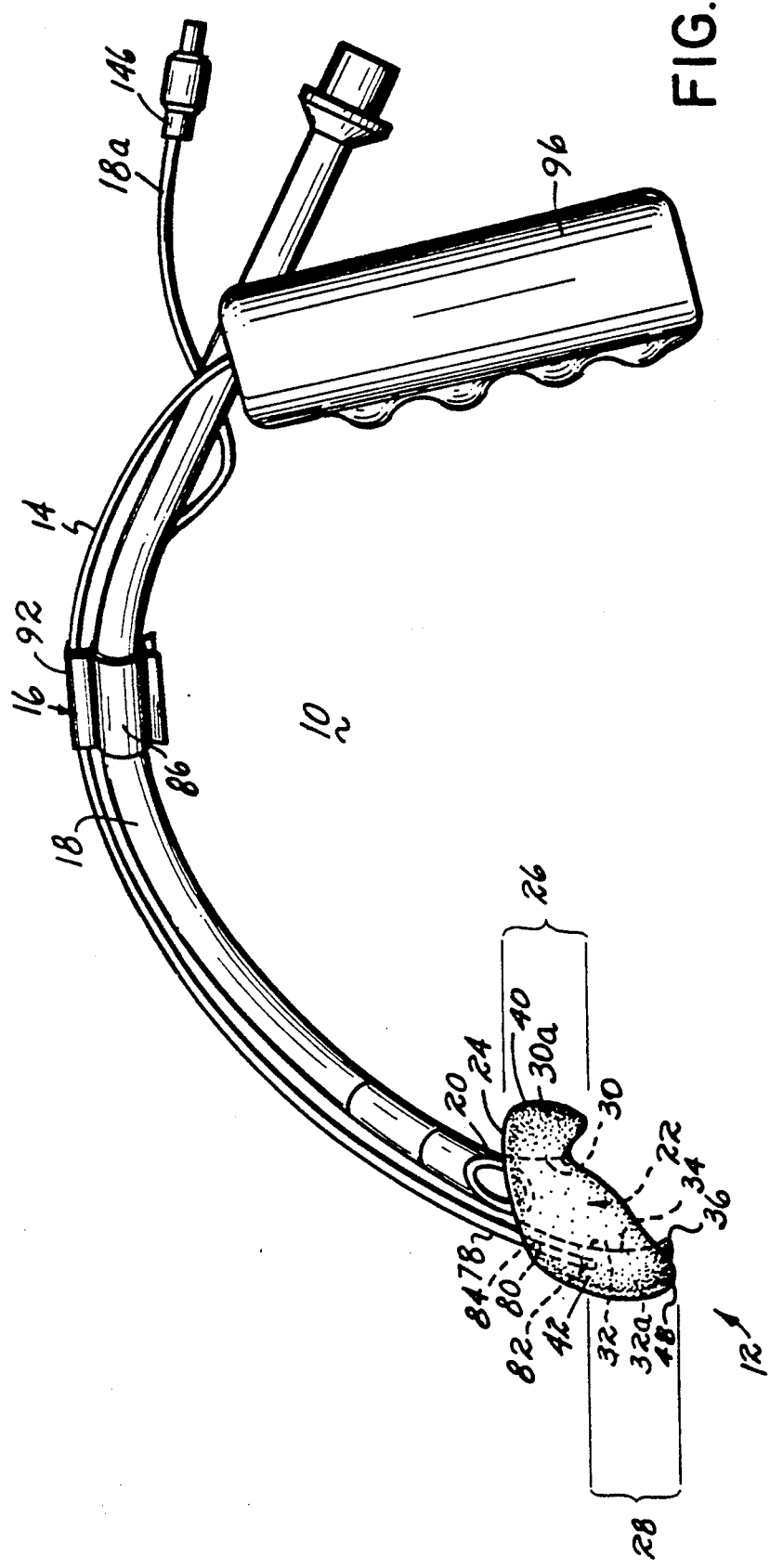
FIG. 1 is a side view of a first embodiment of a medical device according to the principles of the present invention for orotracheal intubation.
Figure 2:
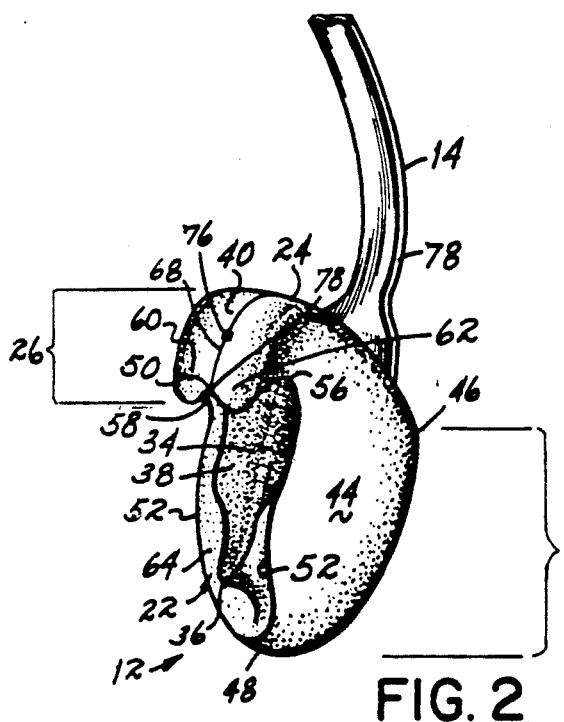
FIG. 2 is a right side, close-up, perspective view of the guide element and blade member distal end of the medical device of FIG. 1.
Figure 3:
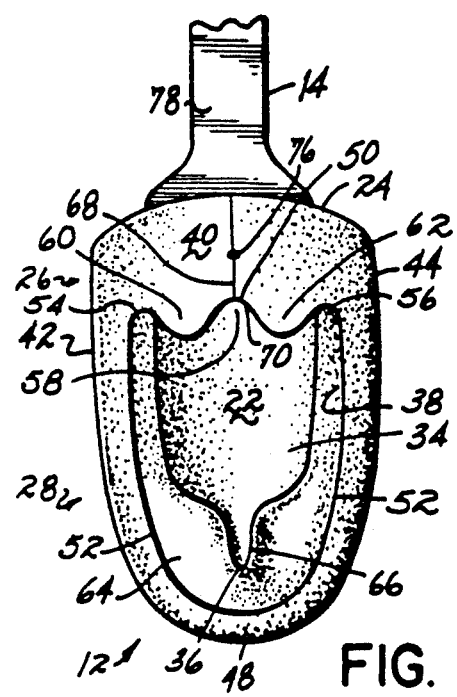
FIG. 3 is a front elevation view of the guide element and blade member distal end of the medical device of FIG. 1.

To assist the reader, included as an Appendix hereto is Table I setting forth the various items discussed herein and their related reference numerals, wherein like numerals in the various Figures refer to the same item.

With reference to FIG. 1, there is shown a medical device 10 for blind orotracheal intubation according to the principles of the present invention. Medical device 10 includes a guide element 12 to which is releasably attached a curved blade member 14. Releasably held against blade member 14 by blade-tube clip 16 is an orotracheal tube 18 with its distal end 20 just entering channel 22 of guide element 12 through top surface 24 thereof. Tube 18 may include a pilot tube 18a as is conventional.

Guide element 12 preferably includes an upper annulus portion 26 through which channel 22 is defined, and a lower body portion 28 depending from the rear of annulus portion 26 posteriorly of channel 22. Channel 22 is defined through annulus portion 26 between an anterior wall 30 and posterior wall 32 both being gently curved in complementary fashion to define anterior and posterior arc portions 30a and 32a to annulus portion 26.

Figure 4:
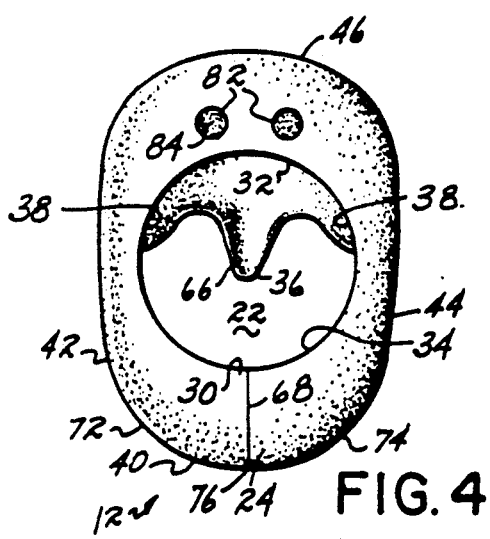
FIG. 4 is a top plan view of the guide element of FIG. 1.

With further reference to FIGS. 2-5, it may be seen that posterior wall 32 of channel 22 extends beyond annulus portion 26 along a curved bearing surface 34 of body 28. Surface 34 preferably terminates in a projecting cusp 36. Posterior and anterior walls 32 and 30 preferably are continuous with channel sidewalls 38 therebetween (FIG. 4).

Depending from upper surface 24 of element 12 are generally smoothly continuous, exterior walls including front wall 40 anteriorly of channel 22, left and right outer walls 42, 44 outboard of channel 22 and curved rear wall 46 posteriorly of channel 22 and surface 34. Walls 40, 42, 44 and 46 cooperate to define exterior contour surfaces to guide element 12. More specifically, side and rear walls 42, 44, 46 merge at the bottom of element 12 to define a generally rounded occluding wall or tip 48 to body portion 28. Front wall 40 terminates in bottom undulating edge 50 which cooperates with continuous edge 52 of sidewalls 42, 44 to define left and right notches 54, 56. Undulating edge 50 of front wall 40 further defines a central notch 58 between a pair of mammillate nodules 60, 62. Guide element 12 further includes interior contour surfaces defined by the anterior wall 30 of channel 22 which merges smoothly into undulating edge 50 and by surface 34, cusp 36 and recess 64 between sidewall edge 52 and edge 66 of surface 34.

Figure 5:
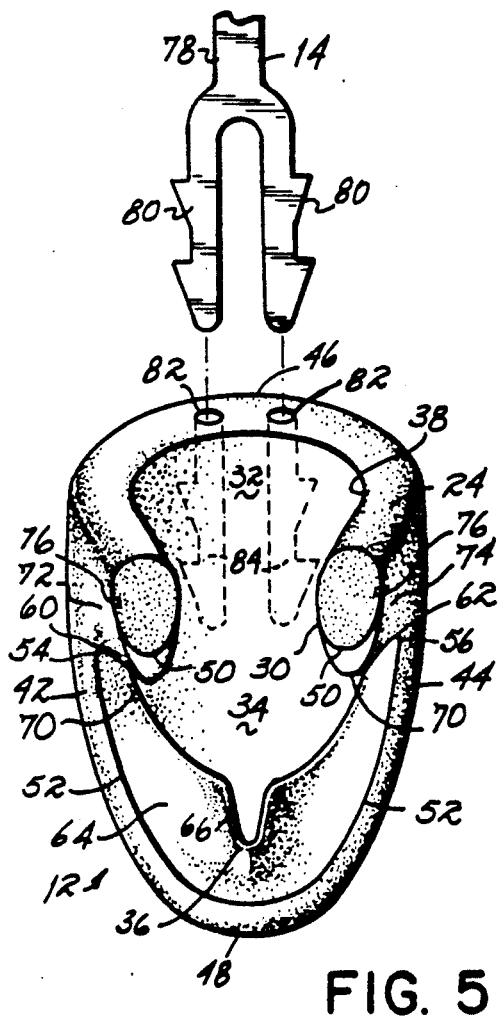
FIG. 5 is a fragmentary, exploded, perspective view of the guide element and blade member distal end of the medical device of FIG. 1.

For access to channel 22 through front wall 40 of annulus portion 26, a slit 68 is preferably provided extending between channel anterior wall 30, guide element front wall 40, upper surface 24, and roof 70 of central notch 58 whereby to define two openable panels 72, 74 of front wall 40 as seen in FIG. 5. Panels 72, 74 are preferably held together by a small portion 76 of front wall 40 to define a tack point. Alternatively, tack point 76 could be comprised of a biologically acceptable glue or similar tacky material placed at the borders of panels 72, 74.

Figure 6:
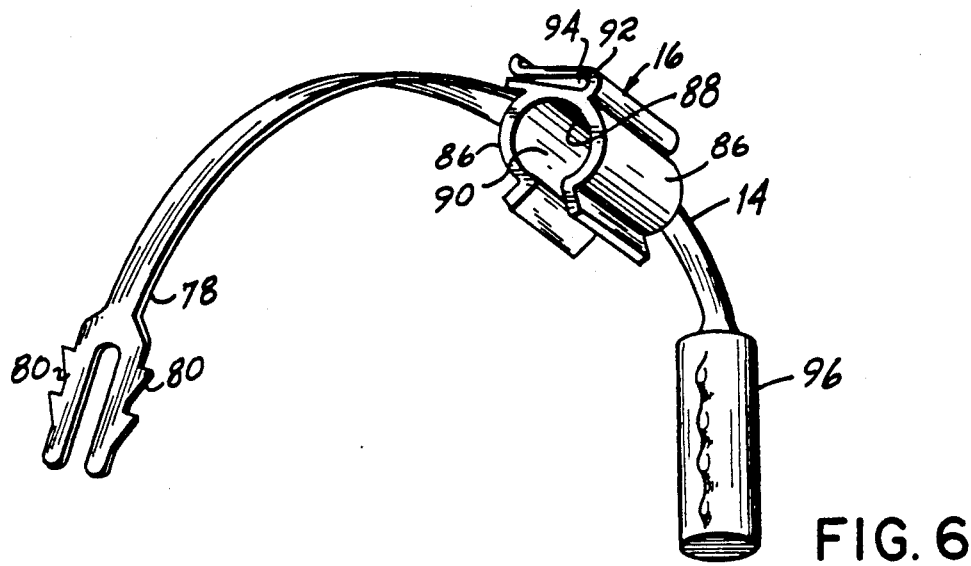
FIG. 6 is a perspective, exploded view of the blade member and blade-tube clip of FIG. 1.

The distal end 78 of blade member 14 is preferably held to element 12 at the rear of the annulus portion 26. To this end, distal end 78 is forked to define a pair of toothed prongs 80 as seen in FIGS. 5 and 6 which are receivable in sockets 82 (FIG. 5) defined through upper surface 24 of element 12 and into body portion 28 thereof. Element 12 is preferably an integral one-piece unit of soft, semi-flexible, high strength silicon rubber, such as Silastic ® HS RTV available from Dow Corning, or other similar material which will not damage the soft tissue of the mouth or throat when manipulated thereagainst as will be described. The silicon rubber body allows for an interference fit of prongs 80 within sockets 82 as represented by dotted lines 84 in FIG. 5.

With further reference to FIG. 6, it may be seen that blade-tube clip 16 is provided with a pair of arcuate spring walls 86 joined at base wall 88 to define a tube-holding space 90. Tube 18 is held by clip 16 by inserting the tube between spring walls 86 a is well understood. Clip 16 is held to member 14 by a resilient flange 92 also joined to base wall 88 to define a generally flat receiving slot 94 into which a flat portion of blade member 14 between distal end 78 and a handle 96 attached to the proximal end thereof is grippingly received.

Figure 7:
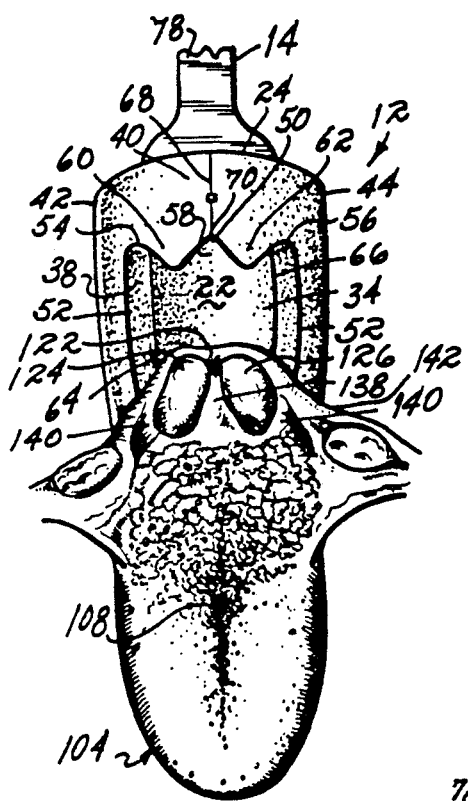
FIG. 7 is a fragmentary, partially schematic view of the guide element and blade member distal end of the medical device of FIG. 1 with the guide element about to be mated with anatomical features, shown in plan-front elevation, at the base of the tongue.
Figure 8:
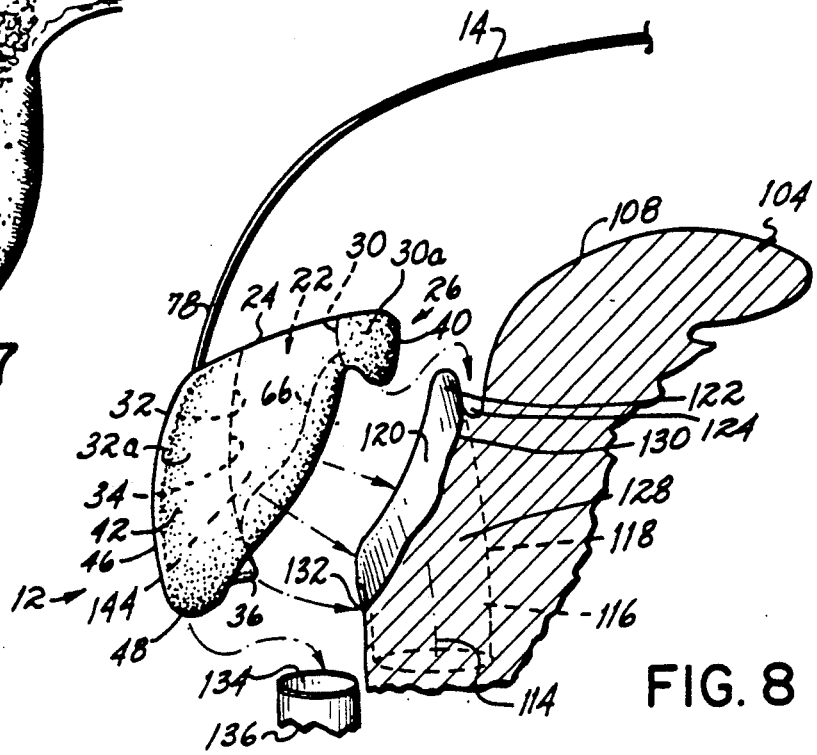
FIG. 8 is a schematic illustration in partial longitudinal cross-section showing the matching of curved inner and outer contours of the curved, beveled edge of the larynx and adjacent structures with the guide element of FIG. 1.
Figure 9:
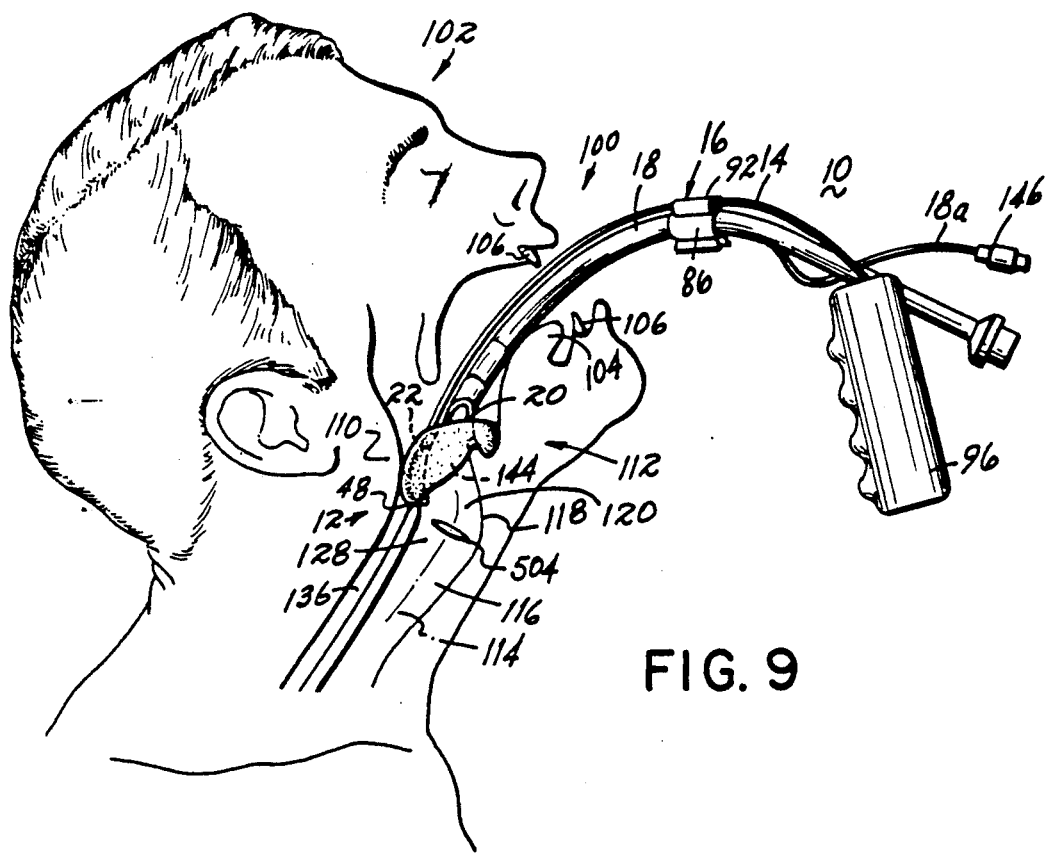
FIG. 9 is a schematic illustration, partially cut-away, showing the medical device of FIG. 1 stabilized in the throat of a patient.

In use, tube 18 is placed into tube-holding space 90 of clip 16 on blade member 14 such that tip end 20 is at least partially within channel 22 but, preferably, not extending below undulating front wall edge 50. Thereafter, handle 96 is manipulated to place guide element 12 into mouth 100 of a patient 102 with guide element rotated such that sidewall 42 or 44 is generally parallel tongue 104 (FIGS. 7-9). Handle 96 is then moved to cause guide element 12 to pass between teeth 106 and over or beside tongue 104. Guide element 12 is advanced in the sideways position until it is past the hump 108 of tongue 104 after which element 12 is turned upright by manipulation of handle 96 exteriorly of mouth 100. Handle 96 is further manipulated to advance guide element 12 along the midline of the mouth toward posterior pharyngeal wall 110 at the back of throat 112 with front wall 40 sliding against tongue 104 and with channel 22 at about a 45° angle to the axis 114 of trachea 116 within larynx 118. Advancement of element 12 into throat 112 will be impeded or stopped by cooperation of one or more of the contour surfaces of element 12 and anatomical features at the back of throat 112 exteriorly of opening 120 into larynx 118. More specifically, element 12 will glide to a stop when:

(a) epiglottis 122 becomes hooked in channel 22 and contacts anterior wall 30 thereof;
(b) mammillate nodules 60, 62 slide into vallecular depressions 124, 126 at the back of tongue 104 and epiglottis 122 and are stopped thereby; and/or
(c) occluding wall or tip 48 butts up against posterior pharyngeal wall 110.

Once this impedance is sensed by the operator, the forward pressure on blade 14 is stopped and, while exerting a gentle downward pressure on blade 14 by manipulation of handle 96 so as to hold mammillate nodules 60, 62 in valleculae 124, 126, which serve as pivots, the lower tip 48 of body portion 28 is rotated forward as far as it will go, which causes channel 22 and surface 34 to become aligned with and to surround laryngeal lumen 128 where the lumen extends above posteriorly beveled edge 130 and behind epiglottis 122 of larynx 118. As seen in FIG. 9, blade member 14 is curved to conform generally to the curvature between mouth 100 and larynx 118 to facilitate such manipulation. The foregoing rotation tends to bring firmly together all the contoured parts of guide element 12 and the matching anatomical features in throat 112. For example, the edge 66 of surface 34 is brought firmly against posteriorly beveled edge 130 of larynx 118 about laryngeal opening 120; the cusp 36 is brought firmly into interarytenoid incisure 132; epiglottis 122 lies tightly against anterior wall 30 of channel 22; lower tip 48 of body portion 28 of guide element 12 is brought directly over the opening 134 of esophagus 136; sidewall edge 52 is brought firmly against the outer surface of edge 130 of larynx 118; central notch 58 is brought firmly astride the median glosso-epiglottic fold 138; and lateral notches 54, 56 are brought firmly astride lateral glosso-epiglottic folds 140 and pharyngo-epiglottic folds 142. Thus, it may be seen that (i) anterior and posterior arc portions 30a, 32a of annulus portion 26 surround the upper axial portion of laryngeal opening 120, and (ii) surface 34 of body portion 28 encloses the lower axial portion of laryngeal opening 120, and tip 48 of body portion 28 substantially occludes esophageal opening 134.

Even though perfect matching of the anatomically contoured surfaces of guide element 12 to anatomical features in throat 112 is not possible, the anatomical mating, i.e., the substantial approximation and interdigitation of these contoured parts with the corresponding anatomical contours, creates a sufficiently smooth tubular structure, with sufficient centering in the hypopharynx and sufficient alignment over the laryngeal opening 120 and sufficient occlusion of adjacent areas of the hypopharynx, to assure accurate, reliable guidance of orotracheal tube 18 exclusively into larynx 118 and trachea 116. Thus, when guide element 12 is properly seated around larynx 118, channel 22 and surface 34 are aligned and continuous with and effectively form an upward continuation of edge 130, epiglottis 122, and lumen 128 of larynx 118 to define a substantially exclusive airway path extension 144 (FIG. 9) atop and coaxial with larynx 118. The airway path extension also functions as a tube guideway thereby aligning distal end 2 of orotracheal tube 18 directly with lumen 128 of larynx 118. Meanwhile, opening 134 into esophagus 136 is occluded by tip 48 of body 28.

The size, annulus portion 26, and generally right-angled shape of guide element 12 help assure that annulus portion 26 will hook onto epiglottis 122 and settle into a secure position around larynx 118, rather than getting lost elsewhere in the hypopharynx or sliding down into esophagus 136. The anatomic contours of the guide element facilitate proper seating of the guide element around the larynx, and a relatively snug circumferential fit around, against and atop the tubular wall of the laryngeal opening, so that there will be no significant gaps between the guide element and larynx through which the tip of the orotracheal tube can migrate on its way through the guide element into the larynx and trachea. Orotracheal tube 18 can thereafter be advanced only into larynx 118 and trachea 116. Pre-lubrication of guide element 12 over its entire surface with a film of sterile, water-soluble medical lubricant, such as Surgilube ® available from Altana, Inc. in Melville, N.Y., minimizes any friction during insertion, mating of contours and passage of orotracheal tube 18.

When the operator senses, by gently but unsuccessfully attempting to move guide element 12 around in a plane perpendicular to the axis of the larynx, that guide element 12 is firmly seated around larynx 118, orotracheal tube 18 may be released from clip 16 and advanced through channel 22 into larynx 118 and trachea 116. Bearing surface 34 of wall 32 and body portion 28 cooperate with annulus portion 26 and channel 22 to confine the travel of orotracheal tube 18 to a smooth, curved pathway leading from mouth 100 directly towards larynx 118 and into laryngeal opening 120 aimed by cusp 36. The remainder of body portion 28 of guide element 12 tends to occupy the hypopharynx and wrap around larynx 118 in such a way as to further isolate the laryngeal lumen and make adjacent areas impassable to an errant orotracheal tube. Once tube 18 is fully inserted, its proximal end 146 may be connected to a respirator (not shown), and the patient's lungs (not shown) ventilated thereby. Guide element 12 may then be withdrawn from throat 112 and mouth 100 by reversing the motion used to insert it therein, leaving orotracheal tube 18 in place in trachea 116. Alternatively, guide element 12 may be withdrawn prior to attaching tube 18 to a respirator. In either case, the entire process of intubation, from the moment guide element 12 is inserted into mouth 100 until the moment when tube 18 is in place in trachea 116 and ready for attachment to a respirator, requires only a few seconds.

After guide element 12 has been withdrawn from mouth 100, annulus portion 26 still surrounds a portion of tube 18. To release tube 18 from the embrace of annulus portion 26, the small tack point 76 is manually broken by pulling the two panels 72, 74 apart at slit 68 to release tube 18 therethrough. Guide element 12 may be removed from blade 14 by forcibly pulling prongs 80 from socket 82. This pulling force causes the silicone rubber sockets 82 to deform sufficiently to release the barbs or teeth of prongs 80. Disposable guide element 12 may then be discarded. If the blade 14, clip 16, and handle 96 are made of a single piece of inexpensive plastic, they may also be discarded.

Figures 10, 11:
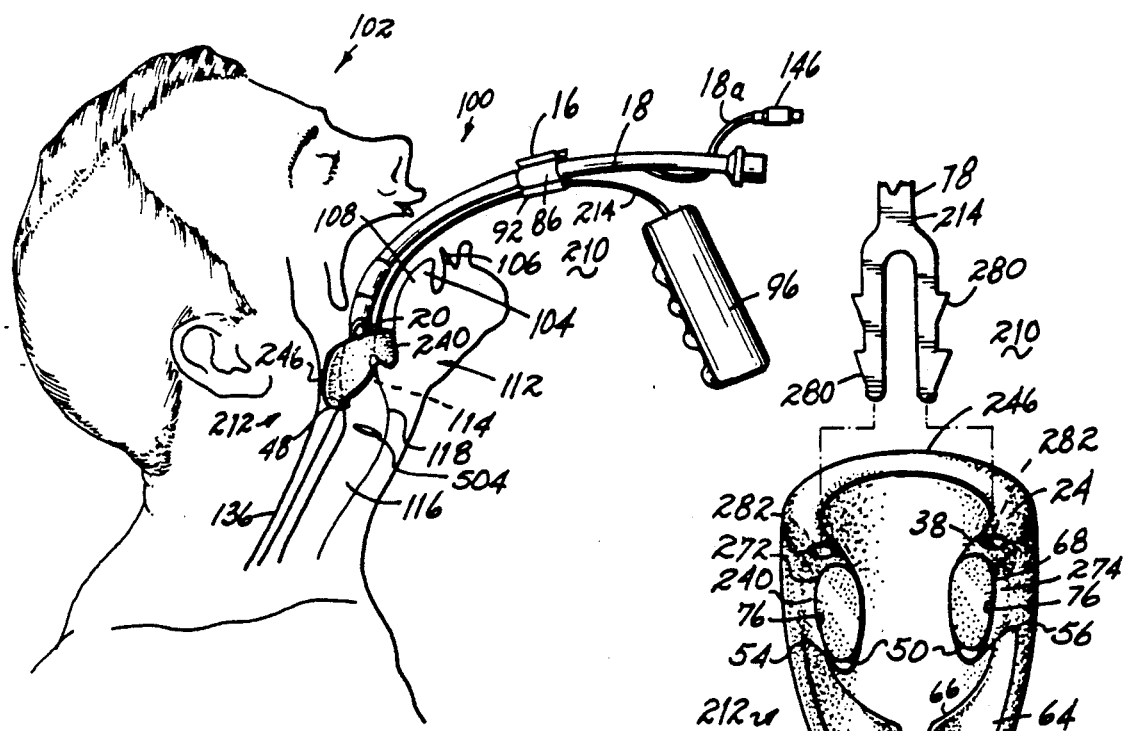
FIG. 10 is a schematic illustration, partially cut-away, showing a second embodiment of a medical device in accordance with the principles of the present invention stabilized in the throat of a patient.
FIG. 11 is a fragmentary, exploded, perspective view of the guide element and blade member distal end of the medical device of FIG. 10.

FIGS. 10 and 11 show a second medical device 210 according to the principles of the present invention. Medical devices 10 and 210 are substantially identical in structure, operation, and use. However, the devices do differ slightly as follows. Blade prongs 280 of blade member 214 fit within sockets 282, one in each of flaps 272, 274 of front wall 240. Clip 16 is mounted to blade member 214 such that orotracheal tube 18 follows over the top of blade member 214 and down into channel 22 rather than from below the blade member as seen in FIG. 1. Front wall 240 of guide element 212 is taller than front wall 40 of element 12 to accommodate receiving prongs 280 of member 214, whereas rear wall 246 of element 212 is shorter than corresponding rear wall 46 of element 12. Blade member 214 is preferably curved to conform generally to the curvature between mouth 100 and larynx 118.

Figure 12:
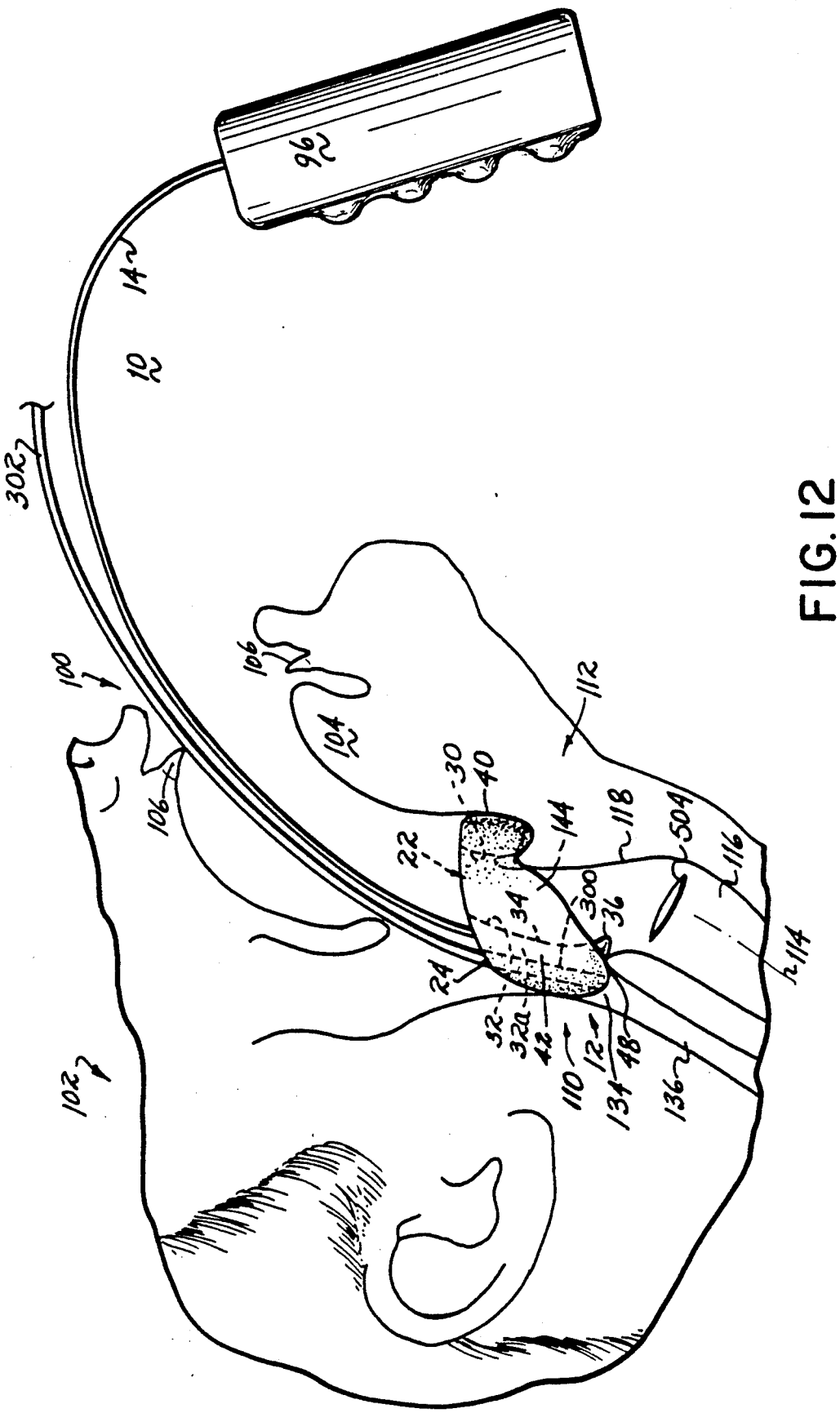
FIG. 12 is a schematic illustration, partially cut-away, showing another embodiment of a medical device in accordance with the principles of the present invention stabilized in the throat of a patient for oroesophageal intubation.

As seen in FIG. 12, medical device 10 (and/or device 210) may include an esophageal tunnel 300 through body portion 28 of guide element 12 (212) and communicating between upper surface 24 and tip 48 for oroesophageal intubation. Tunnel 300 is positioned posteriorly of surface 34 so as not to communicate with channel 22, thus avoiding the creation of a possible misintubation pathway within the guide element. Once the guide element is stabilized in the back of the throat, tunnel 300 defines a path between upper surface 24 and esophageal opening 134. A suction catheter or other similar tubular or elongated member 302 may be received through tunnel 300 for subsequent entry or aiming into esophageal opening 134. During esophageal intubation, airway path extension 144 provided by channel 22 maintains breathability of the patient. Airway path extension 144 may also provide a tubular guideway as in the case of medical devices 10 and 210. To this end, clip 16 may be attached to blade member 14 as shown in FIG. 1 to hold an orotracheal tube 18.

A further embodiment according to the principles of the present invention is medical device 410 for laryngoscopic aiming as shown in FIG. 13. Medical device 410 includes a guide element 412 which is virtually identical to guide element 12, but with the provision of a slant tunnel 500 through annulus portion 26 and body portion 28 terminating as at 502 through posterior wall extension of channel 22 defined by bearing surface 34. Slant tunnel 500 is angled obliquely downward relative channel 22 such that when guide element 412 is stabilized or seated at the back of the patient's throat, tunnel 500 aims at vocal cords 504 within larynx 118. Tunnel 500 also has an entry point 506 adjacent rear wall 46 and upper surface 24 of guide element 412. Tunnel 500 has a diameter slightly larger than the diameter of a fiberbundle 508 of a conventional flexible fiberoptic laryngoscope 510 so as to frictionally engage distal viewing end 512 of fiberbundle 508 therein. Fiberbundle 508 is removable from tunnel 500 by gentle traction.

As is well understood, fiberbundle 508 extends between its distal tip 512 and its body-joining end 514, the latter being connected to body 516 of battery-operated, flexible fiberoptic laryngoscope 510. Scope 510 further includes a battery-containing handle 520 and a viewing eyepiece 522, as is conventional. To hold fiberbundle 508 safely in place, distal tip 512 is preferably passed through a bite-protector clip 524. As seen in FIG. 14, clip 524 is an elongated member having a generally tubular port 526 extending longitudinally therethrough, through which is receivable fiberbundle 508. Clip 524 further includes a generally rectangular port 528 extending longitudinally therethrough and slidably receiving blade member 414 therethrough. Preferably, clip 524 is provided a slot 530 along one edge to permit clip 524 to be slid laterally on or off blade member 414. Clip 524 is preferably made of semi-rigid plastic to protect the fiberbundle, and is covered with a layer of soft pliable plastic material to cushion any contact with the patient's teeth 106.

Figure 15:
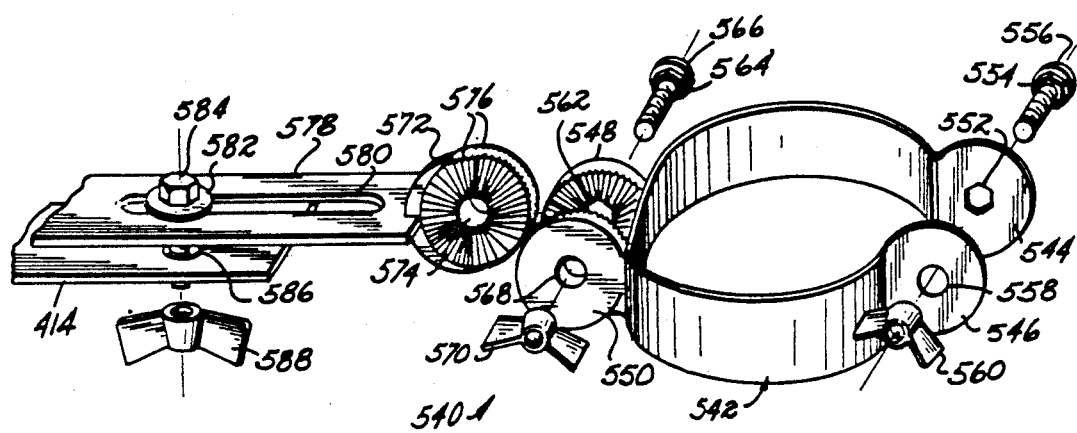
FIG. 15 is a fragmentary, exploded, perspective view of the support of FIG. 13.

Blade member 414 of device 410 is similar to blade member 14, except that a laryngoscope support 540 is provided at blade member proximal end instead of handle 96, as will now be described with reference to FIG. 15. Support 540 includes a semi-flexible circular band 542 configured to surround and hold handle 520 of fiberoptic laryngoscope 510. Band 542 opens in front into a pair of circular, parallel bolt brackets 544, 546, with another pair of circular, parallel bolt brackets 548, 550 attached to the rear. Each of the bolt brackets has a hole through the center thereof for receiving a bolt therethrough. Hole 552 of bracket 544 has a hexagonal shape to receive the non-turning head 554 of threaded bolt 556 therethrough, while hole 558 of bracket 546 is round as is conventional. Brackets 544, 546 are brought together by rotation of wing nut 560 on threaded bolt 556, as is well understood. Similarly, bracket 548 has a hexagonal hole 562 to receive non-turning head 564 of threaded bolt 566 therethrough, the remainder of bolt 566 passing through round hole 568 of bracket 550 to be threadably received into wing nut 570.

Interposed between rear bolt brackets 548, 550 is tongue member 572. Tongue member 572 has a generally circular shape and fits between bolt brackets 548 and 550. Tongue member 572 has a round hole 574 in the center for accepting threaded bolt 566 therethrough. The inner circular faces of rear bolt brackets 548, 550 and both circular faces of tongue member 572 are radially serrated as at 576. Tongue member 572 is attached to horizontal fillet 578 having a longitudinal slot 580 in the center sized to accept in non-rotational relationship non-turning head 582 of threaded bolt 584 which passes downwardly through a hole 586 in the proximal end of blade member 414. Bolt 584 threadably cooperates with wing nut 588 to secure support 540 to blade member 414.

Figure 16:
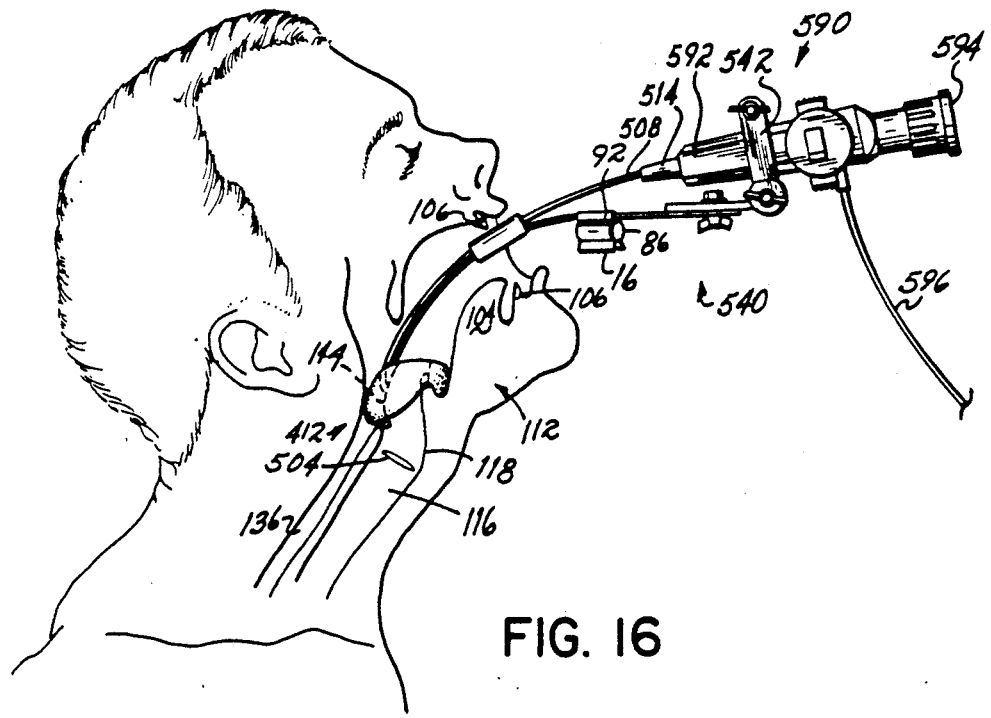
FIG. 16 is a view similar to FIG. 13, but supporting a laryngoscope different from that shown in FIG. 13.

Support 540 may be adjusted as shown in FIG. 13 for laryngoscope 510 or as shown in FIG. 16 for an externally lit laryngoscope 590. As is known, scope 590 includes a control body 592 held by support 540 and directly coupled to source end 514 of fiberbundle 508. Control body 592 also supports an eyepiece 594 and connects to an external light source (not shown) via fiberbundle 596.

To use medical device 410, a guide element 412, with slant tunnel 500 of a diameter slightly larger than that of the fiberbundle which will be inserted into it, is selected and pushed onto blade prongs 80 of blade member 414. If intubation is going to be performed in addition to laryngoscopy, blade tube clip 16 is pushed onto and across blade member 414 from the edge. Bite protector blade clip 524 is also pushed onto blade member 414 from the edge thereof at a point on the blade member where the blade member is likely to be situated between the patient's teeth 106 when guide element 412 is in the throat (see FIG. 13).

The angle of support 540 is adjusted to accommodate the type of flexible fiberoptic laryngoscope to be used. This is accomplished by loosening wing nut 570 on bolt 566, rotating band 542 to the desired vertical angle with respect to fillet 578, and then retightening the wing nut. The radial serrations on bolt brackets 548, 550 and tongue member 572 help maintain this vertical angle and prevent slippage of band 542 out of the rotated position.

The laryngoscope is then secured to blade member 414 by inserting handle 520 into band 542, and then tightening wing nut 560. Next, flexible fiberbundle 508 of laryngoscope 510 is passed, distal tip 512 first, through port 526 of bite protector blade clip 524 and inserted through entry point 506 of tunnel 500 in guide element 412 so that distal tip 512 of the fiberbundle is flush with posterior wall extension 34 of channel 22. To take up any slack in the fiberbundle, the distance from guide element 412 to laryngoscope 510 is adjusted by loosening wing nut 588 on bolt 584, sliding fillet 528 along, or turning it horizontally around, bolt 584 in slot 586, as the case may be, until the desired tightness of the fiberbundle and the desired horizontal angle of the laryngoscope with respect to blade member 414 are achieved, and then retightening wing nut 588. Thereafter, guide element 412 may be inserted into the throat as described in connection with medical device 10.

Similarly, if intubation is to be performed, an orotracheal tube 18 may be included as with medical device 10. When guide element 412 is seated in its proper position around the larynx, distal tip 512 of fiberbundle 508 will be pointed directly at vocal cords 504, and will be stabilized in that position by tunnel 500 which owes its own stability to the matching contours of guide element 412 and anatomical features in throat 112, which enable guide element 412 to attain a secure seat around and against the larynx. The light source of the laryngoscope is then turned on and, looking through eyepiece 522, fine aiming adjustments can then be made by gently manipulating medical device 410 under direct vision. If an orotracheal tube 18 has been secured to blade member 414 as with medical device 10, tube 18 may now be released from blade-tube clip 16 and advanced downward through guide element 412. The distal end 20 of tube 18 can be watched through eyepiece 522 as it approaches and passes between the vocal cords 504, a stable image of which is being transmitted along fiberbundle 508 to eyepiece 522. Thus, visualization of the process of orotracheal intubation, as well as visually-assisted manipulation of other tubular devices within the larynx, are made possible by medical device 410. It can be readily seen that slight variations in the location and angle of slant tunnel 500 within guide element 412 would allow visual and operative access to other areas both within and adjacent the larynx.

Although not shown, blade member 414 could alternatively be coupled to guide element 412 adjacent front wall 40 as in the case of medical device 210 shown in FIGS. 10 and 11. Additionally, an oroesophageal intubation tunnel 300 may be included as in the case of medical device 210. An alternative embodiment of guide element 600 including an oroesophageal tunnel 300 and slant tunnel 500 is shown in FIG. 17 wherein it is seen that tunnel 300 exits tip 48 of guide element 510 as at 602, while slant tunnel 500 exits surface 34 as at 502. Tunnels 300 and 500 are isolated from communication with one another to avoid improper aiming or misintubation.

The guide element for all embodiments of the invention may be made of a soft, high-strength silicone rubber, which is preferably supplied prelubricated over its entire surface with a thin film of biocompatible, water-soluble lubricating gel, and may be contained in a sealed wrapper to protect the lubricating film and to assure cleanliness of the guide element. The blade member, blade tube clip, bite-protector clip, and/or handle can each be made separately of metal or plastic, or can be fabricated together as a single piece of inexpensive, disposable plastic with or without handle 96. Support 540 can also be fabricated in either metal or plastic.

A form for a guide element suitable for a particular size of human or animal throat may be constructed by making a mold around a representative cadaveric larynx (or anatomical model thereof) of the desired size and species which has a relatively large, smooth curved tube inserted into it from the oral cavity. Preferably, the tube has as large an outer diameter as the laryngeal lumen will accommodate. The tube is inserted and extends in a gradual, smooth arc from the interior of the larynx upward and forward toward and into an area defining a mid-portion of the oral cavity. Thereafter, a mold is made around and above the larynx such that the resulting mold incorporates an impression of the anatomy surrounding the larynx. The hardened mold is removed. When the tube is withdrawn from the larynx and the hardened mold, it leaves a cylindrical opening (in the top of the mold) which is continuous posteriorly and inferiorly with a curved central channel (formed by the posterior wall of said tube). The cylindrical opening and the curved central channel form a smooth, continuous, curved pathway leading directly from the mouth downward into the larynx and trachea, along which any tube of smaller diameter (than the original tube) may be blindly guided into the trachea.

The anatomical details of the larynx and surrounding structures and spaces are permanently impressed into the other surfaces of the mold, so that when the mold is removed from the throat and a guide element conforming thereto reinserted into the throat, the guide element can be quickly oriented into position merely by easing it into the hypopharynx. Since the mold represents a three-dimensional negative image of the larynx and hypopharynx, the conforming guide element quickly settles/pops into perfect alignment thereagainst.

To facilitate rapid insertion of the mold (guide element) into the throat, sharp edges and corners can be rounded and reduced in size. Some features may even be eliminated, as long as enough mating detail is maintained to assure a properly oriented and snug fit against the larynx, so that a tube being inserted through the cylindrical opening and into the larynx cannot deviate away from the orotracheal axis and wander into other areas of the hypopharynx. By making a cast from the completed mold, guide elements may be made of any desired material.

Tunnels running from the upper portion of the mold or guide element downward into either the larynx or the esophagus may be drilled or molded as desired.

By virtue of the foregoing, there is thus provided a guiding and aiming device to facilitate blind, gentle, rapid, accurate and selective guiding and aiming of tubular or elongated members relative a patient's larynx and esophagus, especially under emergency conditions. There is thus further provided a guiding and aiming device to facilitate rapid, gentle, and blind oral intubation of the larynx and/or esophagus, without substantial risk of misintubation and without the drawbacks of the prior art. That is, using a guide member according to the principles of this invention, tubular or elongated members may be blindly and selectively aimed or introduced into the laryngeal or esophageal openings, in a rapid, gentle, and accurate manner.

While the present invention has been illustrated by the description of various embodiments and while the embodiments have been described in considerable detail, it is not the intention of applicant to restrict or any way limit the scope of the appended claims to such detail. Additional advantages and modifications will readily appear to those skilled in the art. For example, the medical devices disclosed herein are shown in use in a human throat. The invention has applicability to other animals having a mouth and a larynx, for example. Moreover, the shapes, materials, and arrangements of the components of the various embodiments disclosed herein may be readily altered as necessary. For example, the surface contours of and tunnels within the guide element may be added to or reduced. Similarly, the guide element may be secured to the blade with different configurations of releasably mating connections, or the guide element may be made integral with the blade. The guide element may also be directly attached to the tip of a stylet-type fiberoptic laryngoscope. The guide element may also be made in a skeletal rather than a solid form, or as a collapsible or inflatable device which is expanded or inflated before or after being inserted into the throat. The tack point may also be eliminated and the position of the slit shifted away from the midline of the guide element. The invention in its broader aspects is, therefore, not limited to the specific details, representative apparatus and method, and illustrative examples shown and described. Accordingly, departures may be made from such details without departing from the spirit or scope of applicant's general inventive concept.

TABLE I

APPENDIX

| Reference Number | Item |
| --- | --- |
| 10 | first embodiment of a medical device |
| 12 | guide element of 10 |
| 14 | blade member of 10 |
| 16 | blade-tube clip |
| 18 | orotracheal tube |
| 18a | pilot tube of 18 |
| 20 | distal end of 18 |
| 22 | channel |
| 24 | top surface of 12, 212, 412 |
| 26 | annulus portion of 12, 212, 412 |
| 28 | body portion of 12, 212, 412 |
| 30 | anterior wall of 22 |
| 30a | anterior arc portion of 26 |
| 32 | posterior wall of 22 |
| 32a | posterior arc portion of 26 |
| 34 | extension of wall 22 on surface of 28 |
| 36 | cusp |
| 38 | sidewalls of 22 |
| 40 | front wall of 12, 412 |
| 42 | left outer wall of 12, 212, 412 |
| 44 | right outer wall of 12, 212, 412 |
| 46 | rear wall of 12, 212, 412 |
| 48 | occluding wall or tip of 12, 212, 412 |
| 50 | bottom undulating edge of 40, 240 |
| 52 | edge of 42, 44 |
| 54 | left notch of 12, 212, 412 |
| 56 | right notch of 12, 212 |
| 58 | central notch of 12, 212 |
| 60 | mammillate nodules of 12, 212 |
| 62 | mammillate nodules of 12, 212 |
| 64 | recess of 12, 212 |
| 66 | edge of 34 |
| 68 | slit through 26 |
| 70 | roof of 58 |
| 72 | panel of 40 |
| 74 | panel of 40 |
| 76 | tack point of 68 |
| 78 | distal end of 14 |
| 80 | toothed prongs of 78 |
| 82 | sockets of 12 |
| 84 | interference fit of 80, 82 |
| 86 | spring walls of 16 |
| 88 | base wall of 16 |
| 90 | tube-holding space of 16 |
| 92 | resilient flange of 16 |
| 94 | receiving slot of 16 |
| 96 | handle of 14, 214 |
| 100 | mouth of 102 |
| 102 | patient |
| 104 | tongue of 102 |
| 106 | teeth of 102 |
| 108 | hump of 104 |
| 110 | posterior pharyngeal wall of 102 |
| 112 | throat of 102 |
| 114 | axis of 116 |
| 116 | trachea of 102 |
| 118 | larynx of 102 |
| 120 | opening of 118 |
| 122 | epiglottis of 102 |
| 124 | vallecular depression of 102 |
| 126 | vallecular depression of 102 |
| 128 | lumen of 118 |
| 130 | edge of 118 |
| 132 | interarytenoid incisure of 118 |
| 134 | opening of 136 |
| 136 | esophagus of 102 |
| 138 | median glosso-epiglottic fold of 102 |
| 140 | lateral glosso-epiglottic folds of 102 |
| 142 | pharyngo-epiglottic folds of 102 |
| 144 | airway path |

TABLE I-continued
APPENDIX

| Reference Number | Item |
|---|---|
| 146 | proximal end of 18 |
| 210 | second embodiment of a medical device |
| 212 | guide element of 210 |
| 214 | blade member of 210 |
| 240 | front wall of 212 |
| 246 | rear wall of 212 |
| 280 | blade prop of 214 |
| 282 | sockets of 212 |
| 300 | esophageal tunnel of 12, 212 |
| 302 | esophageal suction catheter |
| 410 | fourth embodiment of medical device |
| 412 | guide element of 410 |
| 414 | blade member of 410 |
| 500 | slant tunnel of 412 |
| 502 | terminus of 500 |
| 504 | vocal cords |
| 506 | entry point of 500 |
| 508 | fiberbundle of 510 |
| 510 | battery-powered laryngoscope |
| 512 | distal tip of 508 |
| 514 | body-joining end of 508 |
| 516 | body of 510 |
| 520 | battery-containing handle of 510 |
| 522 | viewing eyepiece of 510 |
| 524 | bite-protector clip |
| 526 | tubular port of 524 |
| 528 | rectangular port of 524 |
| 530 | slot of 524 |
| 540 | laryngoscope support |
| 542 | band of 540 |
| 544 | bolt bracket of 542 |
| 546 | bolt bracket of 542 |
| 548 | bolt bracket of 542 |
| 550 | bolt bracket of 542 |
| 552 | hole through 544 |
| 554 | head of 556 |
| 556 | bolt |
| 558 | hole through 546 |
| 560 | wing nut |
| 562 | hole through 548 |
| 564 | head of 566 |
| 566 | bolt |
| 568 | hole through 550 |
| 570 | wing nut |
| 572 | tongue member of 540 |
| 574 | hole through 572 |
| 576 | serrated edge of 548, 550, 572 |
| 578 | fillet of 540 |
| 580 | slot in 578 |
| 582 | head of 584 |
| 584 | bolt |
| 586 | hole in 414 |
| 588 | wing nut |
| 590 | externally lit laryngoscope |
| 592 | control body of 590 |
| 594 | eyepiece of 592 |
| 596 | fiberbundle of 590 |
| 600 | alternative embodiment of guide element |
| 602 | tunnel 300 exit of 600 |

What is claimed is:

1. A medical device comprising a guide element receivable through the mouth and into the back of the throat, the guide element having channel wall means for advancing a tube therealong, and contour means cooperable, upon insertion of the guide element into the throat, with anatomical features of and adjacent the larynx for blindly positioning the guide element such that the channel wall means is contiguous with at least the posterior portion of the tubular wall of the laryngeal opening to define an upward extension of at least the posterior portion of the tubular wall of the laryngeal opening whereby a tube advanced along the channel wall means will be directed into the larynx.

2. The medical device of claim 1, the channel wall means including an anterior portion adapted to substantially surround the anterior edge of the laryngeal opening.

3. The medical device of claim 1, the channel wall means including an upper posterior portion and a lower posterior portion, the lower posterior portion of the channel wall means having an edge adapted to substantially abut the posterior and lateral edge of the laryngeal opening.

4. The medical device of claim 3, the contour means including a recessed surface bordering the lower posterior channel wall means edge and adapted to mate substantially gap-free around the posterior and lateral edge of the laryngeal opening.

5. The medical device of claim 3, the contour means including a projecting cusp extending from the lower posterior portion of the channel wall means and adapted to be received in the interarytenoid incisure of the larynx.

6. The medical device of claim 1, the guide element further having occluding means posteriorly of the channel wall means for overlying and substantially occluding the esophageal opening.

7. The medical device of claim 6, the guide element further having esophageal tunnel means through the occluding means for defining a tubular path aimed at the esophageal opening.

8. The medical device of claim 1, the guide element further having an annulus portion with a channel therethrough defined by the channel wall means.

9. The medical device of claim 8, the guide element further having a body portion coupled to the annulus portion posteriorly of the channel and occluding means posteriorly of the channel for overlying and substantially occluding the esophageal opening, the body portion carry the occluding means.

10. The medical device of claim 1, the guide element further having slant tunnel means through the guide element and terminating in the channel wall means for defining a tubular path pointing into the larynx.

11. The medical device of claim 10, the channel wall means including an upper posterior portion and a lower posterior portion, the lower posterior portion having an edge adapted to substantially abut the posterior and lateral edge of the laryngeal opening, the contour means including a recessed surface bordering the lower posterior channel wall means edge and adapted to mate substantially gap-free around the posterior and lateral edge of the laryngeal opening.

12. The medical device of claim 1, the guide element being semi-flexible.

13. The medical device of claim 8, the guide element further having a body portion coupled to the annulus portion posteriorly of the channel, the contour means including at least one of (a) an anterior portion of the channel wall means shaped to receive thereagainst the epiglottis as the guide element is inserted into the back of the throat, (b) valleculae mating means anteriorly of the channel for mating with at least one vallecula as the guide element is inserted into the back of the throat, and (c) tip means at a terminal end of the body portion for stopping the guide element against the posterior pharyngeal wall to prevent over-advancement of the guide element into the throat.

14. The medical device of claim 1 further comprising inserting means coupled to the guide element for blindly inserting the guide element through the mouth and into a position around the larynx by manipulation from outside the mouth.

15. The medical device of claim 17, the inserting means including a member coupled to the guide element and curved to conform generally to the curvature between the mouth and the larynx.

16. The medical device of claim 14, further comprising means for releasably coupling the inserting means to the guide element.

17. The medical device of claim 14, the inserting means including a blade member curved to conform generally to the curvature between the mouth and the larynx and couplable at a distal end to the guide element.

18. The medical device of claim 17, the blade member including a prong on the blade member distal end, the guide element further having socket means therein for receiving the prong.

19. The medical device of claim 18, the socket means being defined in the guide element posteriorly of the channel.

20. The medical device of claim 18, the socket means being defined in the guide element anteriorly of the channel.

21. The medical device of claim 18, the prong having barbs projecting therefrom, the socket means having means for releasably receiving the barbs.

22. The medical device of claim 14 further comprising tube clip means for releasably holding an orotracheal tube or the like to the inserting means.

23. The medical device of claim 22, the tube clip means including means for releasably holding the tube clip means to the inserting means.

24. The medical device of claim 1, the contour means including edge means for mating the guide element around and against the edge of the laryngeal opening, whereby to form a substantially gap-free junction therebetween.

25. The medical device of claim 1, the channel wall means being arcuate so as to extend arcuately up through the throat toward the mouth.

26. A medical device comprising a guide element receivable through the mouth and into the back of the throat, the guide element having an annulus portion with a channel therethrough, the channel having an anterior wall and a posterior wall, the guide element further having a body portion coupled to the annulus portion posteriorly of the channel and supporting a surface defining an extension of the channel posterior wall, the guide element further having means cooperating with anatomical features of and adjacent the larynx for positioning the guide element about the larynx such that the anterior and posterior channel walls effectively form a continuation of the tubular wall of the laryngeal opening into a substantially exclusive airway path extension atop and coaxial the larynx and being substantially gap-free between the airway path extension and the laryngeal opening, the cooperating means defined by at least one of (a) the anterior wall in the channel being shaped to receive thereagainst the epiglottis when the guide element is inserted into the back of the throat, (b) valleculae mating means anteriorly of the channel for mating with at least one vallecula when the guide element is inserted into the back of the throat, (c) tip means at a terminal end of the body portion for stopping advancement of the guide element at the correct depth as the guide element is being inserted into the throat, (d) a central notch in the annulus portion anteriorly of the channel, shaped and positioned to fit over the median glosso-epiglottic fold when the guide element is inserted into the back of the throat, (e) lateral notches in the annulus portion anteriorly of the channel, shaped and positioned to fit over the lateral glosso- and pharyngo-epiglottic folds when the guide element is inserted into the back of the throat, (f) cusp means projecting from the body portion to fit into and above the interarytenoid incisure when the guide element is inserted into the back of the throat, (g) first edge means associated with a posteriorly beveled edge of the larynx when the guide element is inserted into the back of the throat, and (h) second edge means associated with the body portion for fitting around and against the posteriorly beveled edge of the larynx when the guide element is inserted into the back of the throat.

27. The medical device of claim 26, the cooperating means including a plurality of items (a)–(h).

28. The medical device of claim 26 further comprising inserting means coupled to the guide element for manipulating from outside the mouth the guide element in the mouth and throat.

29. The medical device of claim 28 further comprising means for releasably coupling the inserting means to the guide element.

30. The medical device of claim 28, the inserting means including a blade member curved to conform generally to the curvature between the mouth and the larynx and couplable at a distal end to the guide element.

31. The medical device of claim 28 further comprising tube clip means for releasably holding an orotracheal tube or the like to the inserting means.

32. The medical device of claim 31, the tube clip means including means for releasably holding the tube clip means to the inserting means.

33. The medical device of claim 26, the guide element being semi-flexible.

34. The medical device of claim 26, the guide element further having occluding means posteriorly of the channel for overlying and substantially occluding the esophageal opening.

35. The medical device of claim 26, the guide element further having esophageal tunnel means through the body portion for defining a tubular path aimed at the esophageal opening.

36. The medical device of claim 26, the guide element further having slant tunnel means through the guide element and terminating in the airway path extension for defining a tubular path pointing into the larynx.

37. A medical device for blind aiming of a flexible fiberoptic laryngoscope into the larynx comprising a guide element receivable through the mouth and into the back of the throat, the guide element having an annulus portion with a channel defined by a channel wall extending through the annulus portion, contour means cooperating with anatomical features of and adjacent the larynx for positioning the guide element about the larynx such that the channel wall and the tubular wall of the laryngeal opening meet at a substantially gap-free junction therebetween and such that the channel defines a substantially exclusive airway path extension atop and coaxial the larynx, and slant tunnel means extending exterior of the channel through the guide element and terminating in the channel for defining a tubular path pointing obliquely into the laryngeal opening from its posterior aspect.

38. The medical device of claim 37, the slant tunnel means being dimensioned to hold a distal end of a fiberbundle of a fiberoptic laryngoscope whereby to aim the fiberdundle into the larynx.

39. The medical device of claim 38 further comprising an elongated support member having a distal end coupled to the guide element.

40. The medical device of claim 39 further comprising support means associated with a proximal end of the elongate support member for supporting the laryngoscope.

41. The medical device of claim 39 further including means for protecting the laryngoscope fiberbundle passing between the teeth of the patent.

42. The medical device of claim 37, the guide element further having a body portion coupled to the annulus portion posteriorly of the channel, the contour means including at least one of (a) an anterior portion of the channel wall shaped to receive thereagainst the epiglottis as the guide element is inserted into the back of the throat, (b) valleculae mating means anteriorly of the channel for mating with at least one vallecula as the guide element is inserted into the back of the throat, and (c) tip means at a terminal end of the body portion for stopping advancement of the guide element at the correct depth as the guide element is being inserted into the throat.

43. The medical device of claim 37, the guide element further having a body portion coupled to the annulus portion posteriorly of the channel, the body portion including occluding means for overlying and substantially occluding the esophageal opening.

44. The medical device of claim 43, the guide element further including esophageal tunnel means through the body portion and the occluding means for defining a tubular path aimed at the esophageal opening.

45. The medical device of claim 43, the body portion further including a surface defining an extension of a posterior portion of the channel wall.

46. A medical device for blind intubation comprising a guide element receivable through the mouth and into the back of the throat, the guide element having:
   (1) an annulus portion and a body portion depending from the annulus portion, a channel having a posterior wall extending through the annulus portion and along a surface of the body portion and terminating in a projecting cusp;
   (2) contour means defining on the annulus and body portions cooperating with anatomical features at the back of the throat for stabilizing the guide element against the larynx such that the channel is contiguous with at least the posterior edge of the laryngeal lumen and surrounds the posterior and lateral aspects of the laryngeal lumen with the cusp projecting through the interarytenoid incisure, the contour means including (a) an interior wall in the channel shaped to receive thereagainst the epiglottis as the guide element is inserted into the back of the throat, (b) valleculae mating means anteriorly of the channel for mating with at least one vallecula as the guide element is inserted into the back of the throat, and (c) tip means at a terminal end of the body portion for stopping advancement of the guide element at the correct depth as the guide element is being inserted into the throat; and
   (3) surrounding means including the channel walls, the surface of the body portion and the cusp for substantially surrounding the laryngeal opening and embracing the larynx when the channel is aligned with the laryngeal lumen.

47. The medical device of claim 46 further comprising a blade member coupled at a distal end to the guide element.

48. The medical device of claim 47 further comprising means for releasably holding a distal end of an orotracheal tube in the channel.

49. The medical device of claim 48, the body portion being positioned relative to the channel to define a barrier which prevents orally introduced tubular members passing downward through the channel from entering the esophageal opening.

50. The medical device of claim 49, the body portion further being positioned relative the channel such that the tip means substantially occludes the esophageal opening.

51. The medical device of claim 49, the guide element further including tunnel means through the body portion and exiting at the tip means for defining a tubular path aimed at the esophageal opening when the channel is aligned with the laryngeal lumen.

52. The medical device of claim 49, the guide element further having slant tunnel means through the guide element and terminating in the posterior wall of the channel for defining a tubular path pointing into the larynx when the channel is aligned with the laryngeal lumen.

53. The medical device of claim 46, the guide element being semi-flexible.

54. A medical device comprising a guide element sized and shaped to be received through the mouth and into the throat, the guide element having an annulus portion having anterior arc means for engaging the epiglottis and posterior arc means for substantially surrounding the upper axial portion of the laryngeal opening, body portion means adjacent said posterior arc means for substantially enclosing and isolating from surrounding anatomical spaces the lower axial portion of the laryngeal opening, and channel means extending through the annulus portion and along the body portion for guiding an orotracheal tube substantially exclusively into the laryngeal opening.

55. The medical device of claim 54, the guide element further having slant tunnel means therein for stabilizing and aiming the fiberbundle of a fiberoptic laryngoscope.

56. The medical device of claim 54, the guide element further having esophageal tunnel means through the body portion for aiming a tubular-type member substantially exclusively into the esophagus.

57. The medical device of claim 54 further comprising means coupled to the guide element for inserting the guide element into the throat.

58. The medical device of claim 57, the inserting means including a blade member with blade prongs at one end thereof for releasably engaging sockets in the guide element, and handle means at the opposite end of the blade member for manipulating the guide element.

59. A method for blindly and rapidly introducing an orotracheal tube into a patient's trachea comprising:
   providing an airway path extension anatomically contoured to fit about and atop the laryngeal opening;
   inserting the airway path extension through the mouth and into the throat;
   naturally positioning the airway path extension about and atop the laryngeal opening in substantially gap-free contact with the edge of the laryngeal opening whereby to receive an orotracheal tube therethrough and substantially exclusively into the larynx; and advancing an orotracheal tube through the airway path extension whereby the tube advances into the larynx and trachea.

60. The method of claim 59 further comprising removing the airway path extension without removing the orotracheal tube from the larynx.

61. A method for blindly and rapidly introducing an orotracheal tube into a patient's trachea wherein a one-piece guide element having a channel with an upper and a lower end is anatomically contoured to mate substantially gap-free with the edge of the laryngeal opening, the guide element having a tip end posterior to the lower end of the channel and mammillate nodules anterior to the upper end of the channel, the method comprising:

attaching to the guide element a curved blade, the blade having handle means for manipulating the guide element attached to the blade;

placing the distal tip of an orotracheal tube partially within the channel;

inserting the tube-containing guide element into through the patient's mouth and into a position about and atop the laryngeal opening to define a substantially exclusive airway path extension in substantially gap-free contact with the edge of the laryngeal opening by manipulating the blade with the handle means, and advancing the guide element thereby along the upper surface of the tongue with the channel inclined forward approximately 45° from the vertical axis of the trachea until at least one of (i) the channel hooks around the epiglottis, (ii) the tip end impinges against the posterior pharyngeal wall, and (iii) the mammillate nodules slide into corresponding vallecular depressions at the base of the tongue, thereby stopping advancement of the guide element into the throat, and exerting gentle downward pressure on the guide element with the blade while rotating the tip end and channel of the guide element by manipulating the blade so as to bring the channel into alignment with the laryngeal opening whereby to receive an orotracheal tube through the channel and substantially exclusively into the larynx; and advancing an orotracheal tube through the airway path extension whereby the tube advances into the larynx and trachea.

62. The method of claim 61 the guide element further having a surface between the tip end and the lower end of the channel and a cusp projecting from the lower end of the channel, the method further comprising continuing to exert gentle downward pressure on the guide element until the channel substantially surround the epiglottis and laryngeal opening, and so that the surface of the guide element is brought firmly against the posterior edge of the laryngeal opening and the cusp is brought into the interarytenoid incisure, such positioning of the guide element around, against, and atop the edge of the laryngeal opening thereby causing the channel to axially enclose the exposed portion of the laryngeal lumen and to form a substantially continuous, tubular, upward extension of the laryngeal opening into the mouth.

63. The method of claim 61, further comprising releasably securing the tube to the blade before inserting the guide element.

64. The method of claim 63 further comprising releasing the tube from the blade after inserting the guide element.

65. The method of claim 59, further comprising:
providing a tunnel into the airway path pointing at the vocal cords.

66. A method for blindly and rapidly gaining visual access to a patient's larynx through the patient's mouth in preparation for visual observation of orotracheal intubation wherein a one-piece guide element carrying a tunnel and having a channel is anatomically contoured to mate substantially gap-free with the edge of the laryngeal opening, the tunnel being angled relative the channel to point obliquely into the laryngeal opening from its posterior aspect, the guide element having a tip end spaced posteriorly the channel and mammillate nodules space anteriorly the channel, the method comprising:

attaching to the guide element a curved blade, the blade having securing means for securing a fiberoptic laryngoscope to the blade;

securing a fiberoptic laryngoscope having an image guide to the blade;

passing the image guide of the laryngoscope through a bite protector housing mounted on said blade where it passes between the patient's teeth;

inserting a distal tip of the image guide into the tunnel;

placing the distal tip of an orotracheal tube partially within the channel;

inserting the tube-containing guide element through the patient's mouth and into a position about and atop the laryngeal opening to define a substantially exclusive airway path extension in substantially gap-free contact with the edge of the laryngeal opening by manipulating the blade, and advancing the guide element thereby along the upper surface of the tongue with the channel inclined forward approximately 45° from the vertical axis of the trachea until at least one of (i) the channel hooks around the epiglottis, (ii) the tip end impinges against the posterior pharyngeal wall, and (iii) the mammillate nodules slide into corresponding vallecular depressions at the base of the tongue, thereby stopping advancement of the guide element into the throat and exerting gentle downward pressure on the guide element with the blade while rotating the tip end and channel of the guide element by manipulating the blade so as to bring the channel and tunnel into alignment with the laryngeal opening whereby visual access to the larynx is provided by the image guide in the tunnel.

67. The method of claim 66 wherein the larynogoscope includes an eyepiece, the method further comprising:

viewing the vocal cords through the eyepiece;

releasing and advancing the orotracheal tube into the larynx and between the vocal cords and into the trachea while watching these events through the laryngoscope eyepiece.

68. The method of claim 67 further comprising:
removing the guide element without removing the tube; and
removing the fiberoptic image guide from the tunnel by gentle traction.

69. The method of claim 59, providing an esophageal tunnel aimed at the esophageal opening whereby to permit rapid, blind, esophageal access.

70. A guide element to assist in intubating an animal's trachea through the animal's larynx, the guide element having an airway path therethrough, contour means directly cooperating with anatomical contours of and adjacent the larynx upon insertion of the guide element into the throat for blindly positioning the guide element with the airway path coaxial the laryngeal lumen, and means for effectively extending the laryngeal opening exclusively into the airway path when the guide element is so positioned.

71. The guide element of claim 70, wherein said contour means further includes means for positioning the guide element against the larynx such that the airway path and laryngeal opening meet at a substantially gap-free junction.

72. The medical device of claim 1, the guide element further having airway path extension means for defining, when the guide element is positioned by the contoured means, an airway path extension atop and coaxial the laryngeal lumen.

73. The medical device of claim 72, the airway path extension means including an annulus portion with a channel therethrough defined by the channel wall means.

74. The medical device of claim 73, the annulus portion being anatomically contoured so as to cooperate with anatomical features of and surrounding the larynx to position the channel against the laryngeal opening such that the upward extension of the laryngeal wall defined by the channel wall means constitutes the airway path extension atop and coaxial the laryngeal lumen.

75. A method for blindly and rapidly introducing an orotracheal tube from outside the mouth into a patient's trachea comprising:
   inserting a curved channel having a concave bearing surface through the mouth and into the throat;
   while keeping the concave bearing surface oriented toward the oral opening, aligning the channel to extend upwardly from, and with an edge thereof contiguous with, at least the posterior edge of the tubular wall of the laryngeal opening so as to provide an artificial upward extension of the posterior laryngeal wall; and
   advancing an orotracheal tube along the concave bearing surface whereby the tube advances into the larynx and trachea.

76. The method of claim 75 further comprising removing the channel from the throat without removing the orotracheal tube from the larynx.

77. The method of claim 75 further comprising providing a tunnel through the concave bearing surface such that the tunnel points into the larynx when the channel is aligned whereby to permit rapid, blind, stable access of tubular instruments into the larynx.

78. The method of claim 75 further comprising providing an esophageal tunnel carried posteriorly of the channel such that the esophageal tunnel is aimed at the esophageal opening when the channel is aligned whereby to permit rapid, blind oroesophageal access.

* * * * *

UNITED STATES PATENT AND TRADEMARK OFFICE
CERTIFICATE OF CORRECTION

PATENT NO. : 5,038,766

DATED : August 31, 1991

INVENTOR(S) : Jeffrey D. Parker

It is certified that error appears in the above-identified patent and that said Letters Patent is hereby corrected as shown below:

Col. 10, Line 46, "2" should be --20--

Col. 20, Line 11, after "a" add -- posterior wall of the channel for abutting the--

Col. 22, Line 9, "48" should be --46--

Signed and Sealed this

Sixteenth Day of November, 1993

Attest:

BRUCE LEHMAN

*Attesting Officer*  *Commissioner of Patents and Trademarks*